United States Patent [19]
Gibson

[11] Patent Number: 5,508,455
[45] Date of Patent: Apr. 16, 1996

[54] HYDROLYSIS OF METHYL ESTERS FOR PRODUCTION OF FATTY ACIDS

[75] Inventor: Michael S. Gibson, Loveland, Ohio

[73] Assignee: The Procter & Gamble Company, Cincinnati, Ohio

[21] Appl. No.: 324,272

[22] Filed: Oct. 14, 1994

Related U.S. Application Data

[63] Continuation of Ser. No. 108,953, Aug. 18, 1993, abandoned, which is a continuation-in-part of Ser. No. 994,798, Dec. 22, 1992, abandoned.

[51] Int. Cl.$^6$ ......................................................... C11C 1/04
[52] U.S. Cl. ............................................................. 554/160
[58] Field of Search ................................................ 554/160

[56] References Cited

U.S. PATENT DOCUMENTS

| | | |
|---|---|---|
| 601,603 | 3/1898 | Twitchell . |
| 1,068,079 | 7/1913 | Reuter . |
| 1,082,662 | 12/1913 | Twitchell . |
| 1,298,563 | 3/1919 | Reuter . |
| 1,576,005 | 3/1926 | Schrauth . |
| 1,622,974 | 3/1927 | Richardson et al. . |
| 2,042,411 | 5/1936 | Peirce ............................. 87/4 |
| 3,907,884 | 9/1975 | Lynn et al. ...................... 260/542 |
| 4,185,027 | 1/1980 | Logan et al. .................... 260/415 |
| 4,218,386 | 8/1980 | Logan et al. .................... 260/415 |
| 4,747,969 | 5/1988 | Rupilius et al. ................ 260/415 |
| 5,053,535 | 10/1991 | Shima et al. .................... 562/579 |
| 5,128,070 | 7/1992 | Sedelies et al. ................ 554/160 |

FOREIGN PATENT DOCUMENTS

| | | |
|---|---|---|
| 60-058936 | 4/1985 | Japan . |
| 2146638 | 4/1985 | United Kingdom .......... 27/2 |

Primary Examiner—José G. Dees
Assistant Examiner—Samuel Barts
Attorney, Agent, or Firm—Thomas G. Krivulka; Robert B. Aylor; Jerry J. Yetter

[57] ABSTRACT

The present invention relates to an improved process for preparing fatty acids from alkyl, preferably methyl esters via acid hydrolysis by using ratios of water/ester/acid catalyst to form single phase reaction mixtures wherein the initial stoichiometric ratio of water to ester is at least about 1:1. These ratios are represented by the ternary phase diagram of FIG. 1 for a preferred $C_6$–$C_{14}$ alkylbenzene sulfonic acid catalyst having mid-point attachment of the alkyl chain to the benzene ring.

13 Claims, 1 Drawing Sheet

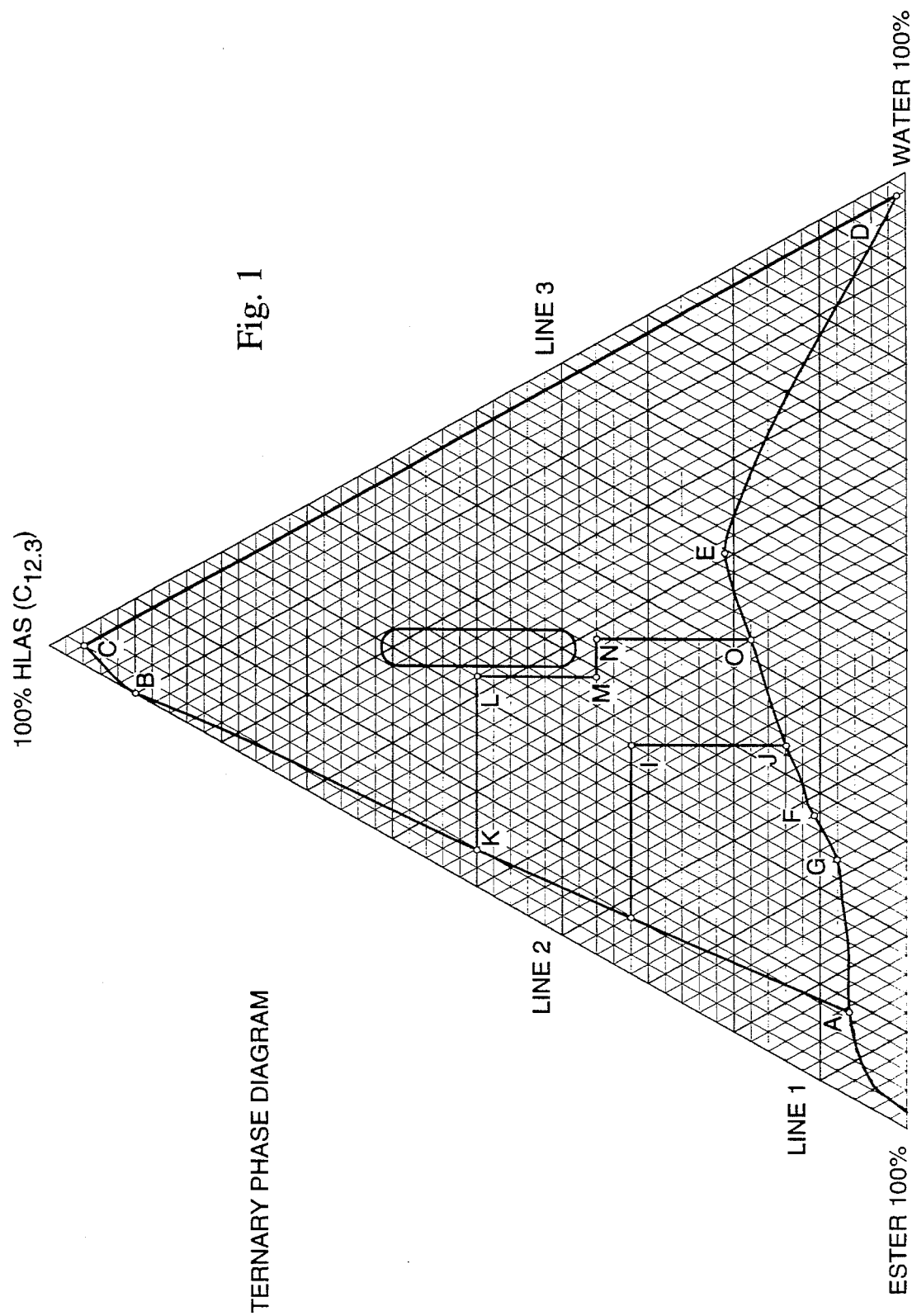

HYDROLYSIS OF METHYL ESTERS FOR PRODUCTION OF FATTY ACIDS

CROSS-REFERENCE TO RELATED APPLICATION

This is a continuation of application Ser. No. 08/108,953, filed on Aug. 18, 1993, now abandoned, which is a continuation-in-part of application Ser. No. 07/994,798, filed on Dec. 22, 1992, now abandoned.

TECHNICAL FIELD

This invention relates to an improved process for hydrolyzing alkyl, preferably methyl esters of fatty acids containing from about 5 to about 20 carbon atoms, preferably from about 5 to about 14 carbon atoms, into the corresponding fatty acids.

BACKGROUND OF THE INVENTION

Several methods for converting fatty acid methyl esters to fatty acids are known.

1. Saponification/Acidulation

This process is outlined below:

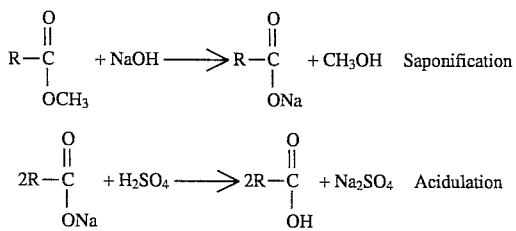

The caustic and acid must be used in excess for achieving maximum conversion of ester to acid. The final product is obtained after washing, drying and distillation of the crude reaction mixture.

Disadvantages of this process include the high cost of processing chemicals, i.e., caustic and sulfuric acid, the slowing of reaction rates with higher carbon chain length feedstock, and formation of intermediates, i.e., soap.

2. Acidolysis

This process involves reacting fatty acid and especially "light cut" fatty acid esters with a short chain carboxylic acid (e.g., propionic acid) in the presence of water and an acid catalyst.

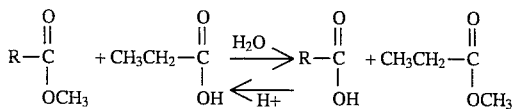

This is a well-known reaction and is described, for example, in Graves U.S. Pat. No. 1,882,808.

Methyl propionate removed from the acidolysis reaction can be reacted with water in the presence of catalyst to yield propionic acid and methanol. Unfortunately, methanol cannot be easily separated from unreacted propionate because of azeotrope formation, which requires costly high energy separation.

Very often, the acidolysis is an acetolysis. The replacing (displacing) acid is acetic acid. In the context of methyl esters of $C_5$–$C_{11}$ carboxylic acids, this means reacting such ester with acetic acid to produce $C_5$–$C_{11}$ carboxylic acids and methyl acetate. This reaction has the disadvantage in a commercial context of requiring disposal or separate hydrolysis of methyl acetate. Disposal is disadvantageous because consumed displacing acid is lost. Separate hydrolysis has the disadvantage of requiring a second process facility (reactor and distillation units different from the reactor and distillation units used for the acetolysis). Also, the acetic acid requires a drying step before it can be reused.

3. Basic Hydrolysis

This process involves splitting methyl esters into fatty acids and methanol at higher temperatures under pressure using catalytic amounts of basic materials. The soap formed initially will serve as emulsifying agent.

The disadvantages of this process are phase separation problems and high pressure operation.

4. Hydrolysis by Water

Conceptually esters can be hydrolyzed without catalyst at high pressures and temperatures, e.g., 700 psig and 250° C. The advantage of this process is that resulting products will not be contaminated with soap, acidic substances or other catalytic materials. The disadvantage is the high cost of equipment needed for high pressure operation.

5. Hydrolysis with Enzymes

Hydrolysis of esters can be promoted with enzymes. Enzymes will act as catalysts by emulsifying and hydrolyzing the reactants. The advantage of this process is that it produces light colored acids. The disadvantage of the process is partial completion of the hydrolysis reaction. In addition, the process control and selection of enzymes will be critical for high catalytic activity.

It is an object of the present invention to provide catalytic hydrolysis of methyl esters utilizing atmospheric pressure. It is a further object of the present invention to provide a process for a single phase hydrolysis reaction which increases the rate of reaction, decreases the number of steps of the reaction, decreases, or eliminates the number of chemical reactants used (i.e., $H_2SO_4$ and NaOH), decreases reaction temperatures, decreases the amount of equipment needed, and recycles the catalyst to reduce processing costs.

SUMMARY OF THE INVENTION

The present invention provides an improved process of preparing fatty acids from alkyl, preferably methyl esters via acid-catalyzed hydrolysis. In the acid hydrolysis process herein, alkyl, preferably methyl, esters of fatty acids are hydrolyzed into the corresponding fatty acids and volatile alcohols in the presence of an acid catalyst having surface active properties, e.g., alkylbenzene sulfonic acid catalyst (HLAS), which is the acid form of a synthetic surfactant. Since the ester and water are normally insoluble, contact between unhydrolyzed ester and water are critical in the process. The surface active acid catalyst of this invention serves to aid the incorporation of water into the ester. The present invention improves acid hydrolysis by using specific ratios of water/ester/acid catalyst to form single phase reaction mixtures wherein the stoichiometric ratio of water to ester is at least about 1:1, and wherein the initial molar ratio of any residual amount of carboxylic acid to ester is less than 1:1, preferably less than 0.5:1, especially when said carboxylic acid contains less than 6 carbon atoms.

Specifically, the process comprises the following steps:

(a) mixing specific ratios of fatty acid ester or mixtures thereof, with water and acid catalyst to form a single phase reaction mixture; and (b) heating the single phase reaction mixture to a temperature of from about 70° C. to about 110° C., wherein the acid catalyst is surface active, heat and water stable; wherein the reaction mixture is essentially free of $C_2$–$C_5$, preferably $C_2$–$C_4$, carboxylic acids (propionic and butyric acid); wherein the initial stoichiometric ratio of water to ester is at least about 1:1; wherein the initial molar ratio of any residual amount of carboxylic acid to ester is less than 1:1, preferably less than 0.5:1, especially when said carboxylic acid contains less than 6 carbon atoms (i.e., valeric acid); and wherein the ratios of acid catalyst/water/ester are the points in the area enclosed by Line 3 in the diagram of FIG. 1, excluding the shaded area, preferably the points in the area enclosed by Line 2, more preferably the points in the area enclosed by Line 1. Line 3 is formed by the straight lines connecting points A (6.5/8.5/85) (catalyst/water/ester), B (90/0/10), C (96/2/2), D (1/97/2), E (21/49.5/29.5), F (11/27/62), G (8/24/68), and A (6.5/8.5/85), excluding the shaded area. Line 2 is formed by the straight lines connecting points A (6.5/8.5/85) (catalyst/water/ester), K (50/4/46), L (50/22/28), M (36/29/35), N (36/33/31), O (18/42/40), F (11/27/62), G (8/24/68), and A (6.5/8.5/85). Line 1 is formed by the straight lines connecting points A (6.5/8.5/85), H (32/6/62), I (32/24/44), J (14/33/53), F (11/27/62), G (8/24/68), and A (6.5/8.5/85). Utilizing single phase reaction mixtures permits the use of lower temperatures, increases the rate of reaction, and decreases the amount of equipment needed to remove water from the system. The reaction is as follows:

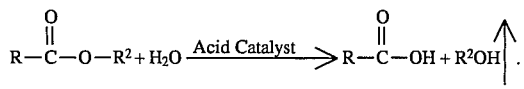

BRIEF DESCRIPTION OF DRAWING

FIG. 1 represents a ternary phase diagram for mixtures of ester, water and HLAS acid catalyst. The ratios of acid catalyst/water/ester, which provide single phase systems, are the points in the area enclosed by Line 3 wherein the initial stoichiometric ratio of water to ester is at least about 1:1, excluding the shaded area, preferably the area enclosed by Line 2, more preferably the area enclosed by Line 1. Line 3 is formed by the straight lines connecting points A (6.5/8.5/85) (catalyst/water/ester), B (90/0/10), C (96/2/2), D (1/97/2), E (21/49.5/29.5), F (11/27/62), G (8/24/68), and A (6.5/8.5/85), excluding the shaded area. Line 2 is formed by the straight lines connecting points A (6.5/8.5/85) (catalyst/water/ester), K (50/4/46), L (50/22/28), M (36/29/35), N (36/33/31), O (18/42/40), F (11/27/62), G (8/24/68), and A (6.5/8.5/85). Line 1 is formed by the straight lines connecting points A (6.5/8.5/85), H (32/6/62), I (32/24/44), J (14/33/53), F (11/27/62), G (8/24/68), and A (6.5/8.5/85).

DETAILED DESCRIPTION OF THE INVENTION

The present invention provides an improved process for preparing fatty acids from alkyl, preferably methyl, esters of fatty acids via-acid-catalyzed hydrolysis. The present invention improves acid hydrolysis by using specific ratios of water/ester/acid catalyst (surface active) to form a single phase reaction mixture wherein the initial stoichiometric ratio of water to ester is at least about 1:1, and wherein the initial molar ratio of any residual amount of carboxylic acid to ester is less than 1:1, preferably less than 0.5:1, especially when said carboxylic acid contains less than 6 carbon atoms.

Specifically, the process comprises the following steps:

(a) mixing specific ratios of fatty acid ester or mixtures thereof, with water and acid catalyst to form a single phase reaction mixture; and (b) heating the single phase reaction mixture to a temperature of from about 70° C. to about 110° C., wherein the acid catalyst is surface active, heat and water stable, wherein the initial stoichiometric ratio of water to ester is at least about 1:1, wherein the initial molar ratio of any residual amount of carboxylic acid to ester is less than 1:1, preferably less than 0.5:1, especially when said carboxylic acid contains less than 6 carbon atoms, and wherein the ratios of acid catalyst/water/ester are the points in the area enclosed by Line 3 in the diagram of FIG. 1, excluding the shaded area, preferably the area enclosed by Line 2, more preferably the area enclosed by Line 1. Line 3 is formed by the straight lines connecting points A (6.5/8.5/85) (catalyst/water/ester), B (90/0/10), C (96/2/2), D (1/97/2), E (21/49.5/29.5), F (11/27/62), G (8/24/68), and A (6.5/8.5/85), excluding the shaded area. Line 2 is formed by the straight lines connecting points A (6.5/8.5/85) (catalyst/water/ester), K (50/4/46), L (50/22/28), M (36/29/35), N (36/33/31), O (18/42/40), F (11/27/62), G (8/24/68), and A (6.5/8.5/85). Line 1 is formed by the straight lines connecting points A (6.5/8.5/85), H (32/6/62), I (32/24/44), J (14/33/53), F (11/27/62), G (8/24/68), and A (6.5/8.5/85).

The following represents the preferred reaction of the present invention:

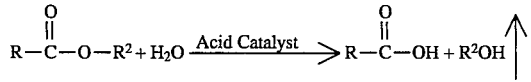

wherein R is a saturated or unsaturated aliphatic chain having from about 5 to about 20, preferably from about 6 to about 14, and more preferably from about 6 to about 12, carbon atoms. $R^2$ is a saturated or unsaturated aliphatic chain having from about 1 to about 4 carbon atoms, and is preferably a methyl group. Methyl esters are preferably used in the process of the present invention because the resulting alcohol is methanol, which is easier to remove. Other esters can be used, especially if the resulting alcohol is useful for the end use of the fatty acid. Examples of suitable methyl esters include methyl caproate, methyl caprylate, methyl caprate, methyl laurate, methyl myristate, methyl myristoleate, methyl palmitate, methyl palmitoleate, methyl stearate, and methyl oleate. The methyl ester reactant herein can be a specific methyl ester or a mixture of different methyl esters. These compounds are insoluble in water. The ester may contain residual amounts of carboxylic acid but the initial molar ratio of this residual carboxylic acid to ester should be less than 1:1, preferably less than 0.5:1, especially when said carboxylic acid contains less than 6 carbon atoms.

Catalyst

An acid catalyst is employed in the process of the present invention. The catalyst used should be surface active (i.e., capable of incorporating the water into the ester phase)

highly acidic, heat and water stable, and be regenerable. The acid catalyst should not be a carboxylic acid since these tend to create the same problems mentioned above for acidolysis reactions.

The preferred catalyst of the present invention is linear alkyl benzene sulfonic acid (HLAS) of the formula:

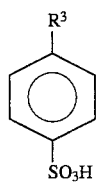

wherein $R^3$ is an alkyl chain having from 1 to about 20 carbon atoms, preferably from about 6 to about 14, more preferably from about 11 to about 13 carbon atoms; and mixtures thereof. This alkyl chain gives the catalyst its surfactant properties.

The $R^3$ group can be attached to the benzene ring at any carbon atom in the alkyl chain. But usually, the alkyl chain is attached to the benzene ring at approximately the middle carbon atom of the alkyl chain. The benzene ring can be substituted.

The acid catalyst of the present invention increases the interfacial activity between two immiscible phases, i.e., water and ester and increases the solubility of water in the organic layer.

The acid catalyst level is typically from about 6% to about 96%, preferably from about 6% to about 20%, more preferably from about 6% to about 15%, by molar weight of the ester. The acid catalyst is preferably recycled during the process. Recycled catalyst can contain from about 0.01% to about 50% fatty acid.

The catalyst (HLAS) in the crude reaction mix can be recovered by simple distillation of the resulting light cut acid away from the reaction mix. This can be accomplished by first removing the unreacted water, traces of methanol, and any unreacted ester via vacuum distillation. The fatty acid product is then distilled under vacuum. The HLAS is left behind in the reaction vessel and can be directly recycled to the reaction. Temperature control is critical in this process to eliminate the decomposition of the catalyst during distillation. Temperatures should be less than about 163° C. (325° F.), preferably less than about 150° C. (302° F.) for the typical HLAS catalyst.

Water

The water in the reaction serves as both a reactant (see overall equation) and as a promoter for the acid-catalyst to speed the reaction. This promoting effect is described in articles by Meade et al. at pages 1–6 of volume 39 of Journal of the American Oil Chemists' Society (January 1962). In general, less water is desirable since any remaining water must be removed. But the initial stoichiometric ratio of water to ester is at least about 1:1 to avoid having to add additional water at a later time.

Generally, the process of the present invention utilizes reaction temperatures of from about 70° C. to about 110° C., preferably from about 95° C. to about 110° C.

The pre-reaction mixture is preferably essentially free of $C_2$–$C_4$ carboxylic acids (propionic and butyric acid) since these may react to form esters which may be more difficult to separate from the fatty acid product. (See Acidolysis, supra.)

The overall reaction is preferably carried out at atmospheric pressure. If desired, subatmospheric or superatmospheric pressures can be utilized. An increase in the pressure will increase water solubility in the ester layer.

The term "fatty acid" is used herein to mean carboxylic acid corresponding to carboxylic acid portion of the ester reactant. Therefore, during the reaction, the ratios represented by the ternary diagram of FIG. 1 remain relatively constant.

The process of the present invention can be carried out as a continuous system or batchwise, and is preferably carried out as a continuous system.

The following examples illustrate, but do not limit, the present invention.

TABLE 1

| Common Name | Carbon Number | Acid MW | Ester MW |
|---|---|---|---|
| Valeric | 5 | 102 | 116 |
| Caproic | 6 | 116 | 130 |
| Caprylic | 8 | 144 | 158 |
| Capric | 10 | 172 | 186 |
| Lauric | 12 | 200 | 214 |
| Myristic | 14 | 228 | 242 |
| Palmitic | 16 | 256 | 270 |
| Stearic | 18 | 284 | 298 |
| Arachidic | 20 | 312 | 326 |

EXAMPLE I

Procedure for Light-Cut Ester Hydrolysis Using HLAS as Catalyst

Following is a batchwise procedure for hydrolyzing light-cut methyl esters.

Chemicals Required (added in this order):
1. About 420 gms methyl ester
2. About 120 gms water, distilled
3. About 60 gms HLAS (with about $C_{12}$ alkyl group with mid chain attachment to phenyl group)

Procedure:
1. Charge 420 gms methyl ester to the reactor. About 50 ml is held out for use in rinsing/diluting catalyst later.
2. Charge 120 gms distilled water to the reactor.
3. Heat the reflux condenser tempered water to about 160° F. (71° C.) on the hot plate and control to that temperature.
4. Start the reflux condenser pumparound loop.
5. Establish cooling water flow to methanol condenser.
6. Set Thermowatch® to 220° F. (104° C.) with Variac® at about 65%.
7. Start agitation at between 400–500 rpm.
8. Heat mixture to about 210° F. (99° C.) while continuing agitation (400–800 rpms).
9. Add 60 gms HLAS and rinse beaker with the ester held out in the beginning.
10. Sample the reactor, recap and continue heating to 220° F. (104° C.).
11. When water begins to reflux, start the reaction timing.
12. Methanol will collect in the side flask. Vapor temperature should be between about 140° and about 180° F. (63° and 82° C.).

13. Take samples from the bottom takeoff stopcock at 30 minute intervals.
14. Monitor and record reaction temperature, vapor temperature, tempered water temperature and stirrer rpm.
15. Silylate samples with bis(trimethylsilyl)trifluoroacetamide in dichloromethane (50/50).
16. Analyze samples by gas chromatograph and plot -LN (conversion) against time. The slope of the resulting line is the rate constant.

After approximately 4 hours, about 97 gms of methanol and 481.8 gms of acid are collected. Thus, conversion is 98.5% in mole percent, with a rate constant, K, of 0.016 min.$^{-1}$. Atmospheric pressure is used.

Procedure for Light-Cut Acid Recovery and HLAS Recycle

1. Place 481.8 gms of the reaction mix from above into a 1,000 ml distillation flask.
2. Distill off water, methanol, and unreacted ester at 250° F. (121° C.) (20 mm Hg).
3. Distill light cut fatty acid away from HLAS at 300° F. (149° C.) (5 mm/Hg).

The above distillation yields 330.8 gms light-cut fatty acid and 72 gms of bottoms including recycled HLAS. The 72 gms of bottoms contains approximately 83.3% HLAS. In general, about 5–10% bottoms cut remain with the HLAS.

EXAMPLE II

Reaction Using Recycled HLAS

The 72 gms of bottoms/HLAS from Example II are recycled and reacted as follows. 7.2 gms of the bottoms/HLAS are removed. 6.0 gms of fresh HLAS are thereafter added.

Chemicals Required (added in this order):
1. 420 gms methyl ester
2. 120 gms water, distilled
3. 60 gms recycled HLAS (with about $C_{12}$ alkyl group with mid chain attachment to phenyl group).

The above weight of components is adjusted to account for the light-cut fatty acid present in the bottoms. The above components are reacted at atmospheric pressure according to the procedure outlined in Example II. After approximately 4 hours, approximately 486.8 gms of acid are collected. Thus, conversion is 97.3% in mole percent, with a rate constant, k, of 0.013 min.$^{-1}$.

Light-Cut Fatty Acid Recovery:
1. Place 486.8 gms of the reaction mix from above into 1,000 ml distillation flask.
2. Distill off water, methanol, and unreacted ester at 220° F. (104° C.) (5 mm Hg).
3. Distill light cut fatty acid away from HLAS at 300° F. (149° C.) (5 mm Hg).

The above distillation yields 59.5 gms of bottoms plus HLAS, and 348.3 gms of light-cut fatty acid.

EXAMPLE III

Approximately the same conversion to fatty acid is accomplished utilizing either fresh HLAS or recycled HLAS.

| Composition | Fresh HLAS Wt. % | Recycled HLAS Wt. % |
|---|---|---|
| $C_8$ Ester | 1.1 | 1.7 |
| $C_{10}$ Ester | 0.8 | 1.3 |
| $C_8$ Acid | 56.9 | 54.6 |
| $C_{10}$ Acid | 40.4 | 41.4 |
| $C_{12}$ Acid | 0.5 | 0.7 |
| Other | 0.3 | 0.3 |
| Total Acid | 97.8 | 96.3 |
| Rate Constant | 0.016min.$^{-1}$ | 0.013min.$^{-1}$ |
| Reaction Time | 240 min. | 240 min. |

EXAMPLE IV

The following is a continuous procedure for hydrolyzing light-cut methyl esters.

Chemicals Required (added in this order):
1. Methyl ester
2. Water, distilled
3. HLAS (with about $C_{12}$ alkyl group with mid chain attachment to phenyl group)

Apparatus:
1. A series of four Continuous Stirred Tank Reactors (CSTR).

Procedure:
1. Prepare a single phase mixture of 70% ester, 20% water, and 10% HLAS and thoroughly mix in a feed tank.
2. Start the reflux condenser pumparound loop and heat to 160°–180° F.
3. Establish cooling water flow to the methanol condensers.
4. Pump the single phase mixture of 70% light-cut ester, 20% water, and 10% HLAS into the first CSTR with continuous heating and agitation (600 rpm).
5. When the mixture reaches the reaction temperature of 100° C., carry the methanol vapors overhead through a partial condenser (160°–180° F.) which refluxes the water back onto the reaction mix. Then flash the methanol through the partial condenser and collect.
6. The reaction mix continues to fill the reactor until it overflows (gravity) into the second reactor which is set up like the first. The reaction is further driven by the lengthened residence time and continuous removal of methanol.
7. The reaction mix then flows through the third and fourth reactors in the same manner with a final conversion of 99%+ to fatty acid.
8. Take samples from a bottom takeoff stopcock as each reactor fills and then at 60 minute intervals after all four reactors are full.
9. Monitor and record reaction temperature, vapor temperature, condenser temperatures and rpm.
10. Flash distill the product either by batch or continuous process to remove the water, unreacted ester, and methanol from the fatty acid/HLAS stream.
11. Flash distill the fatty acid/HLAS stream which separates the two streams. Recycle the HLAS stream back to feed.

EXAMPLE V

| Composition | Reactor 1 (Wt. %) | Reactor 2 (Wt. %) | Reactor 3 (Wt. %) | Reactor 4 (Wt. %) |
|---|---|---|---|---|
| $C_8$ Ester | 9.3 | 3.2 | 1.1 | 0.6 |
| $C_{10}$ Ester | 7.4 | 2.5 | 0.9 | 0.5 |
| $C_8$ Acid | 48.6 | 54.2 | 56.7 | 57.2 |
| $C_{10}$ Acid | 34.7 | 40.1 | 41.3 | 41.7 |
| Totals | 100.0 | 100.0 | 100.0 | 100.0 |
| Reaction time: | ~213 min. | ~426 min. | ~639 min. | ~850 min. |

The above represents the percentage of conversion of ester to acid in each reactor of the continuous process outlined in Example IV.

| Comparison of Fatty Acid Reactions | | | | |
|---|---|---|---|---|
| Run No.: | 1 | 2 | 3 | 4 |
| % HLAS | 1.4 | 2.0 | 10.0 | 10.0 |
| % Ester | 79.0 | 85.0 | 70.0 | 70.0 |
| % Water | 19.6 | 13.0 | 20.0 | 20.0 |
| Composition at 240 Minutes Reaction Time | Wt. % | Wt. % | Wt. % | Wt. % |
| $C_8$ Ester | 4.3 | 4.1 | 1.1 | 1.7 |
| $C_{10}$ Ester | 3.3 | 3.1 | 0.8 | 1.3 |
| $C_8$ Acid | 54.0 | 54.3 | 56.9 | 54.6 |
| $C_{10}$ Acid | 37.5 | 37.6 | 40.4 | 41.4 |
| $C_{12}$ Acid | 0.8 | 0.7 | 0.5 | 0.7 |
| Other | 0.1 | 0.2 | 0.3 | 0.3 |
| Total Acid | 92.3 | 92.6 | 97.8 | 96.3 |
| Phase | 2 | 2 | 1 | 1 |
| Rate Constant: | 0.011 | 0.010 | 0.016 | 0.013 |

EXAMPLE VII

The following ratios of catalyst, water, and esters result in single, double, or triple phase reaction mixtures.

| Example | HLAS (Wt. %) | Water (Wt. %) | Ester (Wt. %) | Phase |
|---|---|---|---|---|
| 1 | 0.0 | 50.0 | 50.0 | 2 |
| 2 | 10.0 | 45.0 | 45.0 | 3 |
| 3 | 20.0 | 40.0 | 40.0 | 1 |
| 4 | 30.0 | 35.0 | 35.0 | 1 |
| 5 | 40.0 | 30.0 | 30.0 | 2 |
| 6 | 50.0 | 25.0 | 25.0 | 2 |
| 7 | 60.0 | 20.0 | 20.0 | 2 |
| 8 | 70.0 | 15.0 | 15.0 | 1 |
| 9 | 80.0 | 10.0 | 10.0 | 1 |
| 10 | 90.0 | 5.0 | 5.0 | 1 |
| 11 | 0.0 | 25.0 | 75.0 | 2 |
| 12 | 10.0 | 20.0 | 70.0 | 1 |
| 13 | 20.0 | 15.0 | 65.0 | 1 |
| 14 | 30.0 | 10.0 | 60.0 | 1 |
| 15 | 40.0 | 5.0 | 55.0 | 1 |
| 16 | 50.0 | 0.0 | 50.0 | 1 |
| 17 | 0.0 | 75.0 | 25.0 | 2 |
| 18 | 10.0 | 70.0 | 20.0 | 2 |
| 19 | 20.0 | 65.0 | 15.0 | 1 |
| 20 | 30.0 | 60.0 | 10.0 | 1 |
| 21 | 40.0 | 55.0 | 5.0 | 1 |
| 22 | 50.0 | 50.0 | 0.0 | 2 |
| 23 | 15.0 | 75.0 | 10.0 | 1 |
| 24 | 10.0 | 60.0 | 30.0 | 3 |
| 25 | 20.0 | 50.0 | 30.0 | 2 |
| 26 | 30.0 | 50.0 | 20.0 | 1 |
| 27 | 40.0 | 45.0 | 15.0 | 1 |
| 28 | 50.0 | 40.0 | 10.0 | 1 |
| 29 | 10.0 | 30.0 | 60.0 | 2 |
| 30 | 25.0 | 25.0 | 50.0 | 1 |
| 31 | 40.0 | 20.0 | 40.0 | 1 |
| 32 | 50.0 | 15.0 | 35.0 | 1 |
| 33 | 65.0 | 17.5 | 17.5 | 1 |
| 34 | 15.0 | 10.0 | 75.0 | 1 |
| 35 | 0.5 | 0.5 | 99.0 | 1 |
| 36 | 0.5 | 1.0 | 98.5 | 1 |
| 37 | 0.5 | 3.0 | 96.5 | 2 |
| 38 | 0.5 | 5.0 | 94.5 | 2 |
| 39 | 1.0 | 0.5 | 98.5 | 1 |
| 40 | 1.0 | 1.0 | 98.0 | 1 |
| 41 | 1.0 | 3.0 | 96.0 | 2 |
| 42 | 1.0 | 5.0 | 94.0 | 2 |
| 43 | 3.0 | 0.5 | 96.5 | 1 |
| 44 | 3.0 | 1.0 | 96.0 | 1 |
| 45 | 3.0 | 3.0 | 94.0 | 2 |
| 46 | 3.0 | 5.0 | 92.0 | 2 |
| 47 | 0.0 | 0.5 | 99.5 | 1 |
| 48 | 0.0 | 1.0 | 99.0 | 2 |
| 49 | 0.0 | 3.3 | 96.7 | 2 |
| 50 | 0.0 | 5.0 | 95.0 | 2 |
| 51 | 0.0 | 30.0 | 70.0 | 2 |
| 52 | 0.0 | 24.0 | 76.0 | 2 |
| 53 | 0.0 | 18.0 | 82.0 | 2 |
| 54 | 0.0 | 12.0 | 88.0 | 2 |
| 55 | 0.0 | 6.0 | 94.0 | 2 |
| 56 | 2.0 | 29.0 | 69.0 | 2 |
| 57 | 2.0 | 23.0 | 75.0 | 2 |
| 58 | 2.0 | 17.0 | 81.0 | 2 |
| 59 | 2.0 | 11.0 | 87.0 | 2 |
| 60 | 2.0 | 5.0 | 93.0 | 2 |
| 61 | 4.0 | 28.0 | 68.0 | 2 |
| 62 | 4.0 | 22.0 | 74.0 | 2 |
| 63 | 4.0 | 16.0 | 80.0 | 2 |
| 64 | 4.0 | 10.0 | 86.0 | 2 |
| 65 | 4.0 | 4.0 | 92.0 | 2 |
| 66 | 6.0 | 27.0 | 67.0 | 2 |
| 67 | 6.0 | 21.0 | 73.0 | 2 |
| 68 | 6.0 | 15.0 | 79.0 | 2 |
| 69 | 6.0 | 9.0 | 85.0 | 2 |
| 70 | 6.0 | 3.0 | 91.0 | 1 |
| 71 | 8.0 | 26.0 | 66.0 | 2 |
| 72 | 8.0 | 20.0 | 72.0 | 1 |
| 73 | 8.0 | 14.0 | 78.0 | 1 |
| 74 | 8.0 | 8.0 | 84.0 | 1 |
| 75 | 8.0 | 2.0 | 90.0 | 1 |
| 76 | 10.0 | 25.0 | 65.0 | 1 |
| 77 | 10.0 | 19.0 | 71.0 | 1 |
| 78 | 10.0 | 13.0 | 77.0 | 1 |
| 79 | 12.0 | 24.0 | 64.0 | 1 |
| 80 | 12.0 | 18.0 | 70.0 | 1 |
| 81 | 12.0 | 12.0 | 76.0 | 1 |

What is claimed is:

1. A process for the production of fatty acids comprising the following steps:

(a) mixing specific ratios of fatty acid ester or mixtures thereof, with water and acid catalyst to form a single phase reaction mixture; and (b) heating the single phase reaction mixture to a temperature of from about 70° C. to about 110° C.;

wherein the acid catalyst is substituted or non-substituted linear alkyl benzene sulfonic acid; wherein the initial stoichiometric ratio of water to ester is at least about 1:1; wherein the initial stoichiometric ratio of any residual amount of carboxylic acid, as a fatty acid ester impurity, to ester is less than 1:1 when said carboxylic acid contains less than 6 carbon atoms; wherein the ratios of acid catalyst/water/ester are the points in the area enclosed by the straight lines connecting points A (6.5/8.5/85) (catalyst/water/ester), B (90/0/10), C (96/2/2), D (1/97/2), E (21/49.5/29.5), F (11/27/62), G (8/24/68), and A (6.5/8.5/85), of FIG. 1, in order, excluding the shaded area, wherein the reaction mixture is essentially free of $C_2$–$C_5$ carboxylic acid, and wherein the fatty acid ester has the formula:

$$R-\overset{\overset{O}{\|}}{C}-O-R^2$$

wherein R is a saturated or unsaturated aliphatic chain having from 5 to 20 carbon atoms, and $R^2$ is a saturated or unsaturated aliphatic chain having from 1 to 4 carbon atoms.

2. The process of claim 1 wherein the ratios of acid catalyst/water/ester are the points in the area enclosed by the straight lines connecting points A (6.5/8.5/85) (catalyst/water/ester), K (50/4/46), L (50/22/28), M (36/29/35), N (36/33/31), O (18/42/40), F (11/27/62), G (8/24/68), and A (6.5/8.5/85) FIG. 1, in order.

3. The process of claim 2 wherein the ratios of catalyst/water/ester are the points in the area enclosed by the straight lines connecting points A (6.5/8.5/85), H (32/6/62), I (32/24/44), J (14/33/53), F (11/27/62), G (8/24/68), and A (6.5/8.5/85) FIG. 1, in order.

4. The process of claim 3 wherein the temperature of (b) is from about 95° C. to about 110° C.

5. The process of claim 1 wherein R is from about 6 to about 14 carbon atoms, and $R^2$ is from about 1 to 2 carbon atoms.

6. The process of claim 5 wherein R is from 6 to about 12 carbon atoms, and $R^2$ is a methyl group.

7. The process of claim 1 wherein the acid catalyst is recovered from the reaction mixture by the following steps:

(a) distilling the unreacted water, methanol and unreacted ester under vacuum; and (b) distilling the fatty acid product away from the product of (a) under vacuum.

8. The process of claim 7 wherein the temperature does not exceed about 163° C. (325° F.) for reaction mixtures containing $C_8$–$C_{12}$ fatty acids.

9. The process of claim 8 wherein the temperature does not exceed about 150° C. (302° F.).

10. A process for the production of fatty acids comprising the following steps:

(a) mixing specific ratios of fatty acid ester or mixtures thereof, with water and acid catalyst to form a single phase reaction mixture; and (b) heating the single phase reaction mixture to a temperature of from about 70° C. to about 110° C.;

wherein the reaction mixture is essentially free of $C_2$–$C_5$ carboxylic acid, wherein the initial stoichiometric ratio of water to ester is at least about 1:1; wherein the initial stoichiometric ratio of any residual amount of carboxylic acid, as a fatty acid ester impurity, to ester is less than 1:1 when said carboxylic acid contains less than 6 carbon atoms; wherein the ratios of acid catalyst/water/ester are the points in the area enclosed by the straight lines connecting points A (6.5/8.5/85) (catalyst/water/ester), B (90/0/10), C (96/2/2), D (1/97/2), E (21/49.5/29.5), F (11/27/62), G (8/24/68), and A (6.5/8.5/85), of FIG. 1, in order, excluding the shaded area; the acid catalyst is a substituted or non-substituted linear alkyl benzene sulfonic acid of the formula:

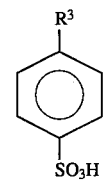

wherein $R^3$ is an alkyl group having from 1 to 20 carbon atoms, and mixtures thereof, and wherein the fatty acid ester has the formula:

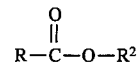

wherein R is a saturated or unsaturated aliphatic chain having from 5 to 20 carbon atoms, and $R_2$ is a saturated or unsaturated aliphatic chain having from 1 to 4 carbon atoms.

11. The process of claim 10 wherein $R^3$ is an alkyl group with from about 6 to 14 carbon atoms, and mixtures thereof.

12. The process of claim 11 wherein $R^3$ is an alkyl group having from about 11 to 13 carbon atoms, and mixtures thereof.

13. The process of claim 10 wherein the $R^3$ group is attached to the benzene ring. at the middle one-half of the alkyl chain.

* * * * *